United States Patent
Xi et al.

(10) Patent No.: US 9,732,610 B2
(45) Date of Patent: Aug. 15, 2017

(54) METHOD OF SAMPLING OIL-BEARING INCLUSION

(71) Applicants: China Petroleum & Chemical Corporation, Beijing (CN); China Petroleum & Chemical Corporation Exploration & Production Research Institute, Beijing (CN)

(72) Inventors: Binbin Xi, Beijing (CN); Weijun Shi, Beijing (CN); Hong Jiang, Beijing (CN); Jianzhong Qin, Beijing (CN); Jin Xu, Beijing (CN); Yuanyuan Ma, Beijing (CN); Zhiming Li, Beijing (CN); Xiaolu Yu, Beijing (CN); Jun Zhang, Beijing (CN)

(73) Assignees: CHINA PETROLEUM & CHEMICAL CORPORATION, Beijing (CN); CHINA PETROLEUM & CHEMICAL CORPORATION EXPLORATION & PRODUCTION RESEARCH INSTITUTE, Beijing (CN)

( * ) Notice: Subject to any disclaimer, the term of this patent is extended or adjusted under 35 U.S.C. 154(b) by 263 days.

(21) Appl. No.: 14/567,447

(22) Filed: Dec. 11, 2014

(65) Prior Publication Data
US 2015/0168358 A1 Jun. 18, 2015

(30) Foreign Application Priority Data
Dec. 16, 2013 (CN) .......................... 2013 1 0690418

(51) Int. Cl.
*G01N 30/14* (2006.01)
*G01N 30/72* (2006.01)
(Continued)

(52) U.S. Cl.
CPC ............. *E21B 49/02* (2013.01); *G01N 30/06* (2013.01); *G01N 30/7206* (2013.01); *G01N 2030/065* (2013.01)

(58) Field of Classification Search
CPC .. E21B 49/02; G01N 2030/065; G01N 30/06; G01N 30/7206
See application file for complete search history.

(56) References Cited

U.S. PATENT DOCUMENTS

2012/0079894 A1    4/2012 Van Berkel et al.

FOREIGN PATENT DOCUMENTS

CN          102455317 A      5/2012
CN          101726556 B      7/2012
(Continued)

OTHER PUBLICATIONS

I-Ming Chou et al., "A new method for synthesizing fluid inclusions in fused silica capillaries containing organic and inorganic material" Geochimica et Cosmochimica Acta (2008), vol. 72, Issue 21, pp. 5217-5231, (available online Aug. 26, 2008).
(Continued)

*Primary Examiner* — Daniel S Larkin
(74) *Attorney, Agent, or Firm* — Novick, Kim & Lee, PLLC; Allen Xue

(57) ABSTRACT

A method of sampling ingredients of an oil-bearing inclusion includes a) providing a first container and a second container, an external diameter of the first container being smaller than an internal diameter of the second container, and the first and second containers both being transparent; b) adding a solvent into the first container and sealing said first container; c) adding an oil-bearing inclusion sample into the second container, and putting the first container that contains the solvent and is sealed in step b) into the second container; and d) using a laser to ablate the oil-bearing inclusion sample contained in the second container that is sealed in step c), and using the laser to break an end portion of the first container close to the sample on condition that the second container is maintained complete, so as to allow the solvent in the first container to enter the second container.

10 Claims, 6 Drawing Sheets

(51) Int. Cl.
*E21B 49/02* (2006.01)
*G01N 30/06* (2006.01)

(56) References Cited

FOREIGN PATENT DOCUMENTS

| CN | 102879331 A | 1/2013 |
|---|---|---|
| JP | 7-333145 A | 12/1995 |

OTHER PUBLICATIONS

Liang Kan et al., "Present Status and Development Trend of Experimental Analysis of Hydrocarbon Fluid Inclusion" Special Oil & Gas Reser Voirs, ISSN: 1006-6535, vol. 19 Issue 5, Oct. 10, 2012.
I-Ming Chou et al., "A new optical capillary cell for spectroscopic studies of geologic fluids at pressures up to 100 MPa" Advances in High-pressure Technology for Geophysical Applications (2005), pp. 475-485.
Xiao-Hong Sun et al., "Composition Determination of Single Fluid Inclusions in Salt Minerals by Laser Ablation ICP-MS" Chinese Journal of Analytical Chemistry (2013), vol. 41, Issue 2, Feb. 2013, pp. 235-241.
Bin-Bin Xi et al., "Using Laser Raman Microprobe and Fused Silica Capillaries to Determine Salinity of Fluid Inclusions" Rock and Mineral Analysis (2013), vol. 32, Issue 1, Feb. 2013, pp. 34-39.

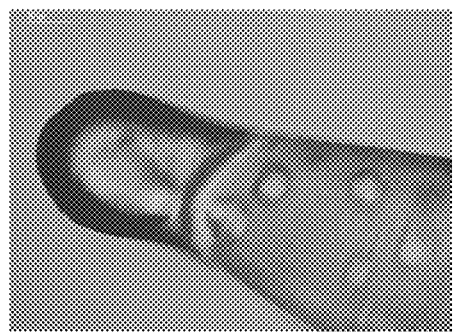
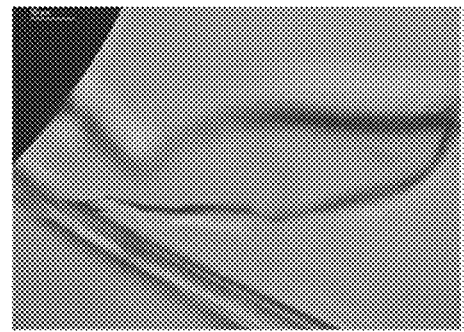
Fig. 3(a)  Fig. 3(b)
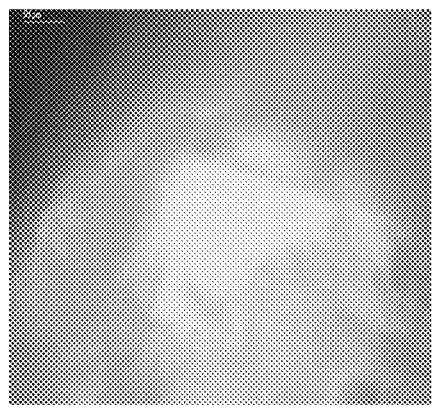
Fig. 4(a)  Fig. 4(b)

METHOD OF SAMPLING OIL-BEARING INCLUSION

CROSS-REFERENCE TO RELATED APPLICATIONS

The present application claims benefit of Chinese patent application CN 201310690418.5 filed on Dec. 16, 2013, the entirety of which is incorporated herein by reference.

FIELD OF THE INVENTION

The present disclosure relates to field of oil and gas exploration and research, and is used for collecting gradients of oil-bearing inclusions contained in geological samples.

BACKGROUND OF THE INVENTION

Oil-bearing inclusions are samples of ancient geological fluids captured in minerals such as calcite, quartz, and the like in oil and gas charging and entrapment processes. Analysis into the ingredients of the oil-bearing inclusions is one of the most important means to learn the properties, sources, entrapment periods, and the like of the oil and gas. However, because individual inclusions per se are relatively small (generally having a diameter smaller than 20 μm) and oil-bearing inclusions formed at different periods often co-exist in one and the same mineral grain, it is a key and difficult point in analyzing ingredients of inclusions to effectively collect the ingredients in target inclusions. In the prior art, two steps are generally performed to collect ingredients of oil-bearing inclusions. In the first step, the main minerals around the inclusions are destroyed to release the ingredients thereof, and in the second step, the released ingredients of the inclusions are extracted and gathered. The main minerals around the inclusions can be destroyed mainly by the procedures of laser ablation, mechanical disruption, and thermal cracking. Among these procedures, laser ablation is of high accuracy and can destroy the main minerals around the inclusions at the level of a micrometer scale, and thus can selectively release the ingredients of the inclusions. However, ingredients of the inclusions cannot be selectively released through mechanical disruption or thermal cracking, which would destroy the main minerals around non-target inclusions while trying to destroy the main minerals around target inclusions. Consequently, collected ingredients would be contaminated. Extraction and enrichment of the ingredients of inclusions are mainly performed by two methods: (1) carrier gas blowing and cold trap enrichment and (2) solvent extraction enrichment. Through method (1), although gaseous hydrocarbons and low to medium carbon liquid hydrocarbons in the inclusions can be effetely extracted, as the number of carbon atoms in the compounds of the inclusion increases, the extraction efficiency would constantly decrease. Moreover, due to complexity of the extraction apparatus, large amounts of contaminations would be introduced from outside. On the other hand, method (2) has quite low extraction efficiency of gaseous hydrocarbons, although liquid hydrocarbons (liquid hydrocarbon having relatively large numbers of carbon atoms) can be effectively extracted. As can be concluded, through the existing methods, gaseous hydrocarbons and a part of low carbon liquid hydrocarbons contained in the target inclusions can be effectively gathered. As to high carbon compounds in the target oil-bearing inclusions, however, high collection efficiency and effective reduction of contaminations from outside cannot be guaranteed.

SUMMARY OF THE INVENTION

In view of the technical state in the prior art as described above, in order to eliminate the defects that the existing methods cannot effectively collect compounds with large numbers of carbon atoms contained in target oil-bearing inclusions and that contaminations are easily introduced from outside, the present disclosure provides a method of sampling ingredients of an oil-bearing inclusion, comprising:

a) providing a first container and a second container, an external diameter of the first container being smaller than an internal diameter of the second container;

b) adding a solvent into the first container and sealing said first container;

c) adding an oil-bearing inclusion sample into the second container, putting the first container that contains the solvent and is sealed in step b) into the second container, and then sealing the second container; and d) using a laser to ablate the oil-bearing inclusion sample contained in the second container that is sealed in step c), so as to release ingredients of the oil-bearing inclusion therein, and then using the laser to break an end portion of the first container close to the sample on condition that the second container is maintained complete, so as to allow the solvent in the first container to enter the second container, thus dissolving the ingredients of said oil-bearing inclusion sufficiently into the solvent.

In one preferred embodiment of the present disclosure, the material of the first and second containers can be at least one selected from a group consisting of organic polymers and inorganic glass.

Said organic polymer can be at least one selected from a group consisting of polymethylmethacrylate, polypropylene, polycarbonate, polyethylene, polyamide, and polystyrene, while said inorganic glass can be at least one selected from a group consisting of ordinary glass and/or quartz glass, preferably quartz glass.

In one preferred embodiment of the method according to the present disclosure, a cross section of the first container or the second container is in the shape of any one selected from a group consisting of triangles, ovals, circles, semicircles, and polygons, preferably a square.

In one preferred embodiment of the method according to the present disclosure, a hydrogen flame gun is used in step b) and step c) for sealing the first or second container.

In one preferred embodiment of the method according to the present disclosure, sail solvent used in step b) is at least one selected from a group consisting of n-hexane, n-heptane, isooctane, isopropanol, dichloromethane, cyclohexane, benzene, toluene, freon, trichloromethane, and ether, preferably h-hexane.

In one preferred embodiment of the method according to the present disclosure, said solvent used in step b) is injected into the first container by a chromatography syringe, and then centrifuged to reach an end portion of the first container by a centrifuge, and frozen into a solid, followed by vacuum seal of the first container.

In one preferred embodiment of the method according to the present disclosure, the solvent in the first container is centrifuged using a centrifuge so as to enter an end of the second container where the sample is placed in step d).

In one preferred embodiment of the present disclosure, said second container is processed, e.g. being fired by a hydrogen flame gun, at a place between the oil-bearing inclusion sample on said container and an end of the first container close to said sample, so as to form an internal depression structure at said place of the second container. As such, when the organic solvent is subsequently being centrifuged by a centrifuge to reach the end of the first container close to the sample, the first container would be prevented from being centrifuged to reach the end close to the sample as well, which would otherwise disturb solvent extraction of the sample. In addition, the second container can be broken at the place of the depression structure, which would facilitate readily extraction of the liquid contained therein without being disturbed by the first container.

In one preferred embodiment of the method of the present disclosure, the oil-bearing inclusion sample obtained in step d) is analyzed with a geochemical instrument, preferably analyzed with a gas chromatograph-mass spectrometer.

In one preferred embodiment of the present disclosure, the schematic drawing of a rock sample and the solvent of the present disclosure after being sealed is shown in FIG. 1. In this embodiment, a double-layer square capillary structure is used, which not only ensures relative independence of the sample and the solvent of n-hexane, but also allows them to be placed in one and the same enclosed space. Furthermore, compared with a circular capillary tube, a better effect can be observed in a square capillary tube under a microscopically.

Technical Effects of the Present Disclosure

The method of the present disclosure can be simply and conveniently operated. Use of a multi-layer square capillary tube structure not only ensures relative independence of the sample and the solvent, but also allows them to be placed in one and the same enclosed space. Besides, a high accurate excimer laser can specifically ablate the target inclusions, thus effectively reducing contaminations introduced from outside. Moreover, the organic solvent extraction used in the present disclosure is in favor of enrichment of ingredients with large numbers of carbon atoms of the inclusions. Compared with the prior art, the method provided by the present disclosure can satisfy the requirements of effective collection of compounds with large numbers of carbon atoms in the target oil-bearing inclusions and at the same time reduce contaminations introduced from the outside.

BRIEF DESCRIPTION OF THE DRAWINGS

FIG. 3(a) is an image of a first square quartz capillary tube before being ablated as enlarged by 200 times;

FIG. 3(b) is an image of the first square quartz capillary tube after being ablated as enlarged by 200 times;

FIG. 4(a) is an image of an inclusion from LUO well No. 63 before being ablated as enlarged by 200 times;

FIG. 4(b) is an image of the inclusion from LUO well No. 63 after being ablated as enlarged by 200 times;

In the drawings, the same reference numbers are used for the same components.

DETAILED DESCRIPTION OF THE EMBODIMENTS

Figure 1:
FIG. 1 schematically shows a method of sampling ingredients of an oil-bearing inclusion according to Example 1 of the present disclosure.

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, group of elements, components, and/or groups thereof.

Language such as "including," "comprising," "having," "containing," or "involving," and variations thereof, is intended to be broad and encompass the subject matter listed thereafter, as well as equivalents, and additional subject matter not recited. Further, whenever a composition, a group of elements, process or method steps, or any other expression is preceded by the transitional phrase "comprising," "including," or "containing," it is understood that it is also contemplated herein the same composition, group of elements, process or method steps or any other expression with transitional phrases "consisting essentially of," "consisting of," or "selected from the group of consisting of," preceding the recitation of the composition, the group of elements, process or method steps or any other expression.

The corresponding structures, materials, acts, and equivalents of all means or step plus function elements in the claims, if applicable, are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiments described herein were chosen and described in order to best explain the principles of the present disclosure and the practical application, and to enable others of ordinary skill in the art to understand the present disclosure for various embodiments with various modifications as are suited to the particular use contemplated. Accordingly, while the present disclosure has been described in terms of embodiments, those of skill in the art will recognize that the present disclosure can be practiced with modifications and in the spirit and scope of the appended claims.

Reference will now be made in detail to the specific subject matter disclosed. Although the subject matter disclosed will be described in connection with the claims as listed below, it can be understood that the subject matter is not to be limited by the claims. In contrast, the disclosed subject matter covers all alternatives, variations, and equivalents, which may be contained in the subject matter defined by the claims.

The present disclosure will be explained in more details with reference to examples, which are not intended to limit the scope of the present disclosure.

An ingredient analyzer GC(7890A)-MS(5975C) by Agilent Technologies was used for gas chromatography-mass spectrometry analysis of ingredients of oil-bearing inclusions in the examples.

The chromatographic conditions were as follows: a chromatographic column model of DB-5 ms, a specification of 30 m×0.32 mm×0.25 μm, a temperature of 300° C. at a sample inlet, and a temperature of 300° C. in a transmission line. The chromatographic column was heated by temperature programming which read: 80° C. (3 min)–3° C./min→210° C.–2° C./min→310° C. (15 min). Helium gas was used as the carrier gas at a flow rate of 1.5 ml/min with splitless injection. In the mass spectrum, EI+ was used as the ion source, and the scan was performed at the mode of TIC with a scan of 50 u to 800 u and SIM with m/z 123, 191, 217 and 221.

An OH100 hydrogen flame gun produced by Walker Energy Equipment Co., Ltd was used, with a highest temperature of 2,800° C. reachable.

An IEC MB centrifuge produced by Block Scientific, Inc. with a rated speed of 14,000 rpm was employed.

A GEO-Laser (193 nm laser) produced by Coherent was used.

Example 1

This example was performed in the following steps.

(1) A certain amount of calcitecement sample 1 in a brecciated fracture zone of LUO well No. 63 in Zhanhua Sag was weighed and smashed with a mortar into particles having a across area less than 1 mm×1 mm. The particles were then dried and washed with a solvent to remove hydrocarbon ingredients absorbed on a surface thereof.

(2) Two square quartz capillary tubes were selected, a first square quartz capillary tube 4 having an internal diameter of 0.7 mm×0.7 mm, an external diameter of 0.9 mm×0.9 mm, and a length of about 50 mm, while a second square quartz capillary tube 2 having an internal diameter of 1 mm×1 mm, an external diameter of 1.2 mm×1.2 mm, and a length of about 60 mm. The two square tubes were first put into a dichloromethane solvent and soaked for 48 hours, then taken out, and dried. A hydrogen flame gun was used to close off one end of both of the two square tubes, which were then put into a dryer to be baked for about 30 min at 100° C. and removed of moisture contained therein.

(3) About 10 ul of n-hexane 3 was injected into the first square quartz capillary tube 4 with a chromatographic syringe and then centrifuged to reach a sealing end with a centrifuge. One open end of the first square quartz capillary tube 4 was afterwards connected into a vacuum pump, and the other end thereof was soaked into liquid nitrogen so as to freeze the n-hexane contained therein into a solid. The vacuum pump was started to vacuum pump the first square quartz capillary tube 4, which was finally sealed at the end close to the vacuum pump by the flame gun and then taken out from the liquid nitrogen.

(4) A sample was first added into the second square quartz capillary tube 2, and then the first square quartz capillary tube 4 was put into the second square quartz capillary tube 2. After that, the flame gun was used to seal off an open end of the second square quartz capillary tube 2 (to obtain a structure as shown in FIG. 1). The second square quartz capillary tube 2 was then put under laser lens to find the target inclusion in the sample 1, the ingredients of which were to be collected. The main minerals around the target inclusion in the sample 1 were ablated with a 193 nm excimer laser, so as to release the ingredients of the inclusion contained therein. After the ablation of the target inclusion was completed, the 193 nm excimer laser was used to break the first square quartz capillary tube 4 at an end thereof close to the sample. The second square quartz capillary tube 2 was then put into a centrifuge to allow the n-hexane 3 therein to be centrifuged and reach the end close to the sample.

(5) Relevant experimental analysis was performed of the ingredients of the oil-bearing inclusion by a gas chromatograph-mass spectrometer.

Through the above process, the released ingredients of the inclusion were sufficiently dissolved into the solvent of n-hexane. Ingredient analysis can be implemented only by breaking the second square quartz capillary tube 2 to take out the solution contained therein.

The image of the first square quartz capillary tube 4 at the end close to the sample before and after being ablated by the laser are shown in FIGS. 3(a) and 3(b) respectively. The 193 nm laser can ablate the first square quartz capillary tube 4 at the end close to the sample, so as to release the solvent of n-hexane contained therein.

Figure 5:
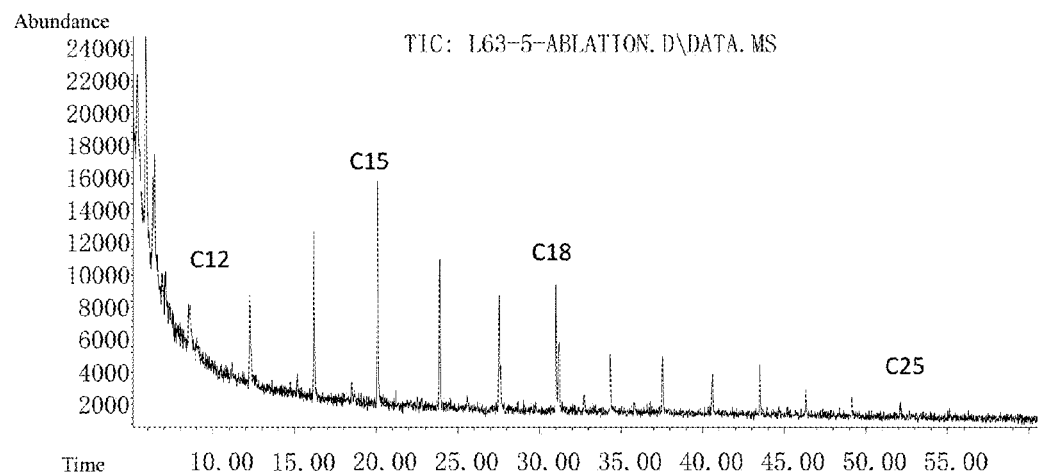
FIG. 5 shows an analysis result of ingredients of the inclusion from LUO well No. 63 by gas chromatography-mass spectrometry.

Through comparisons between the photographs as shown in FIGS. 4(a) and 4(b) taken before and after the sample was ablated respectively, it can be seen that the inclusions in the sample were selectively ablated, without affecting other inclusions around. The analysis result of the sample as shown FIG. 5 indicates that the hydrocarbon ingredients in the inclusions mainly comprise n-alkanes, with C15 as the main peak carbon and C25 as the highest carbon that can be tested. The hydrocarbons contained in the inclusions were relatively light, indicating that light oils or gas condensates were captured in the inclusions.

Example 2

Another oil-bearing inclusion was analyzed about the ingredients thereof. Before that, background ingredients (i.e., ingredients collected in the same way in which the ingredients of the inclusion of the present disclosure were collected except that the main minerals around the inclusion were not ablated) of a sample of the inclusion were collected and analyzed, with the result thereof shown in FIG. 6.

After collection and analysis of the background ingredients, the same sample was used to perform collection and analysis of ingredients contained therein.

This example was implemented in the following steps.

(1) A sample 1 was smashed with a mortar into particles having a cross section less than 1 mm×1 mm. The particles were then dried and washed with a solvent to remove hydrocarbon ingredients absorbed on a surface thereof.

(2) Two square quartz capillary tubes were selected, a first square quartz capillary tube 4 having an internal diameter of 0.7 mm×0.7 mm, an external diameter of 0.9 mm×0.9 mm, and a length of about 50 mm, while a second square quartz capillary tube 2 having an internal diameter of 1 mm×1 mm, an external diameter of 1.2 mm×1.2 mm, and a length of about 80 mm. The two square tubes were first put into a dichloromethane solvent and soaked for 48 hours, then taken out, and dried. A hydrogen flame gun was used to close off one end of both of the two square quartz capillary tubes. After one end of the second square quartz capillary tube 2 was sealed, it was fired for 2 s by the hydrogen flame gun at a place 20 mm away from the sealing end, so as to allow the firing place to be inwardly recessed by approximately 0.2 mm. As such, when the n-hexane was subsequently centrifuged by a centrifuge to reach the end close to the sample in step (4), the first square quartz capillary tube 4 would be prevented from being centrifuged to reach the end close to the sample as well, which would otherwise disturb solvent extraction of the sample. In addition, the second square quartz capillary tube 2 can be broken at the firing place, which would facilitate readily extraction of the solution contained therein without being disturbed by the first square quartz capillary tube. The two square tubes were finally placed into a dryer to be baked for about 30 min at 100° C. and removed of moisture contained therein.

(3) About 10 ul of n-hexane 3 was injected into the first square quartz capillary tube 4 with a chromatographic syringe and then centrifuged to reach a sealing end with a centrifuge. One open end of the first square quartz capillary tube 4 was afterwards connected into a vacuum pump, and the other end thereof was soaked into liquid nitrogen so as to freeze the n-hexane 3 contained therein into a solid. The vacuum pump was started to vacuum pump the first square quartz capillary tube 4, which was finally sealed at the end close to the vacuum pump by the flame gun and then taken out from the liquid nitrogen.

Figure 2:
FIG. 2 schematically shows a method of sampling ingredients of an oil-bearing inclusion according to Example 2 of the present disclosure.

(4) A sample was first added into the second square quartz capillary tube 2, and then the first square quartz capillary tube 4 was put into the second square quartz capillary tube 2. After that, the flame gun was used to seal off an open end of the second square quartz capillary tube 2 (to obtain a structure as shown in FIG. 2). The second square quartz capillary tube 2 was then put under laser lens to find the target inclusion in the sample 1, the ingredients of which were to be collected. The main minerals around target inclusion in the sample 1 were ablated with a 193 nm excimer laser, so as to release the ingredients of the inclusion. After the ablation of the target inclusion was completed, the 193 nm excimer laser was used to break the first square quartz capillary tube 4 at an end thereof close to the sample. The second square quartz capillary tube 2 was then put into a centrifuge to allow the n-hexane 3 therein to be centrifuged and reach the end close to the sample.

(5) Relevant experimental analysis was performed of the ingredients of the oil-bearing inclusion by a gas chromatograph-mass spectrometer.

Through the above process, the released ingredients of the inclusion were sufficiently dissolved into the solvent of n-hexane. Ingredient analysis can be implemented only by breaking the second square quartz capillary tube 2 to draw out the solution contained therein.

Figure 7:
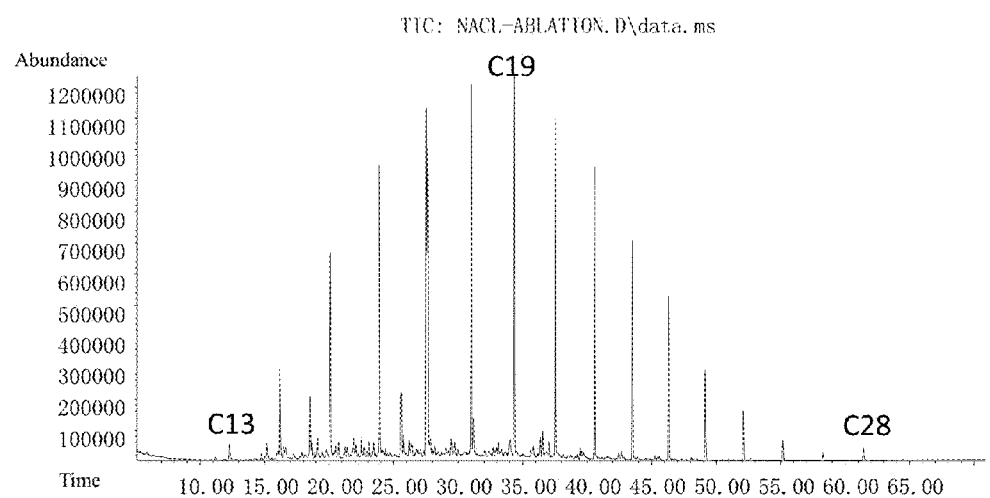
FIG. 7 shows an analysis result of ingredients of the inclusion in Example 2 by gas chromatography-mass spectrometry, the ingredients being collected according to the method of the present disclosure.

The sample obtained was analyzed and the result thereof was shown in FIG. 7.

Figure 6:
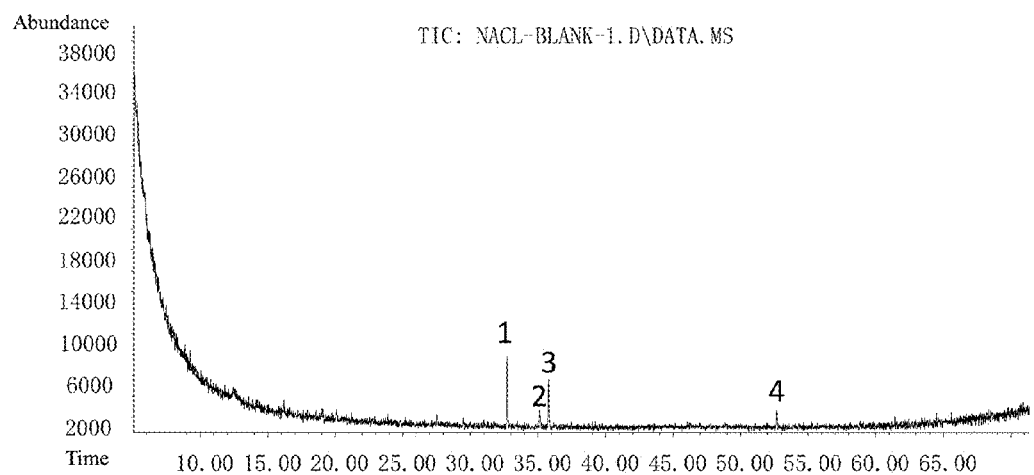
FIG. 6 shows an analysis result of ingredients of the inclusion in Example 2 by gas chromatography-mass spectrometry, the ingredients being collected as background ingredients.

Through comparisons between FIGS. 6 and 7, it can be seen that the background ingredient analysis result has both smaller numbers of impurity peaks (peaks numbered 1 to 4 as shown in FIG. 6) and lower response strength (the strength of the highest peak 1 was only 10,000 as shown in FIG. 6) than the ingredient analysis result of the inclusion, which indicates a relatively small influence imposed on the analysis result by contaminations introduced by the method per se.

Example 3

An ingredient analyzer GC(7890A)-MS(5975C) by Agilent Technologies (the analyzer used here in this example was the same as that used in Example 1 or 2, but the analysis conditions of this example were different from those of Example 1 or 2) and a comprehensive two-dimensional gas chromatography-time-of-flight mass spectrometer, Pegasus 4D by LECO Corporation were used for gas chromatography-mass spectrometry analysis of ingredients of an oil-bearing inclusion in this example.

The chromatographic conditions of the gas chromatograph-mass spectrometer were as follows: a chromatographic column model of DB-5 ms, a specification of 30 m×0.32 mm×0.25 μm, a temperature of 300° C. at a sample inlet, and a temperature of 300° C. in a transmission line. The chromatographic column was heated by temperature programming which read: 60° C. (2 min)–50° C./min→140° C.–3° C./min→300° C. (10 min). Helium gas was used as the carrier gas at a flow rate of 1.5 ml/min without split stream sampling. In the mass spectrum, EI+ was used as the ion source at a temperature of 230° C., and the scan was performed at the mode of SIM. The scan ions include m/z 83, 105, 123, 134, 170, 183, 192, 217, and 231.

Two chromatographic columns were used by the comprehensive two-dimensional gas chromatography-time-of-flight mass spectrometer: a one-dimensional chromatographic column with a model of DB-Petro and a specification of 50 m×0.2 mm×0.5 μm; a two-dimensional chromatographic column with a model of DB-17HT, a specification of 2.1 m×0.1 mm×0.1 μm. The chromatographic conditions were as follows: a temperature of 290° C. at a sample inlet, and a temperature of 290° C. in a transmission line. The one-dimensional chromatographic column was heated by temperature programming which read: 35° C. (3 min)–5° C./min→150° C.–3° C./min→305° C. (30 min). The two-dimensional chromatographic column had a temperature 10° C. higher than the one-dimensional chromatographic column, and the modulator had a temperature 15° C. higher than the two-dimensional chromatographic column. The modulation period was 10 s, with 2.5 s of cold blowing and 2.5 s of hot blowing. Helium gas was used as the carrier gas at a flow rate of 1.5 ml/min with splitless injection. In the mass spectrum, the temperature of the ion source was 200° C. and the scan was performed at the mode of full scan with a scan scope of ions in the range from 50 to 600 u.

The ingredients of an oil-bearing inclusion taken from well T901 in Tahe Oilfield were analyzed according to the method as recited in Example 1. Before collecting and analyzing the ingredients of the oil-bearing inclusion, background ingredients (i.e., ingredients collected in the same way in which the ingredients of the inclusion of the present disclosure were collected except that the main minerals around the inclusion were not ablated) of the target inclusion in the sample 1 were collected and analyzed.

Figure 8:
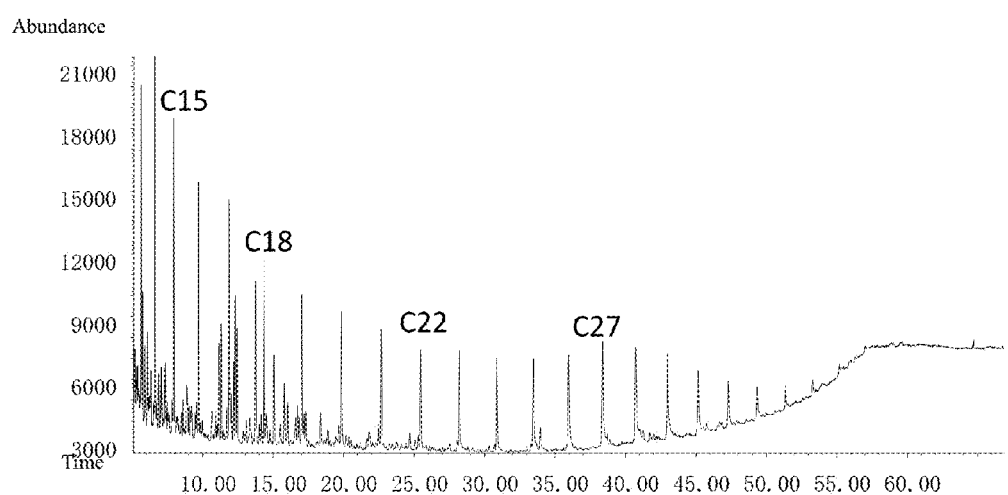
FIG. 8 shows an analysis result of ingredients of the inclusion in Example 3 by gas chromatography-mass spectrometry.
Figure 9:
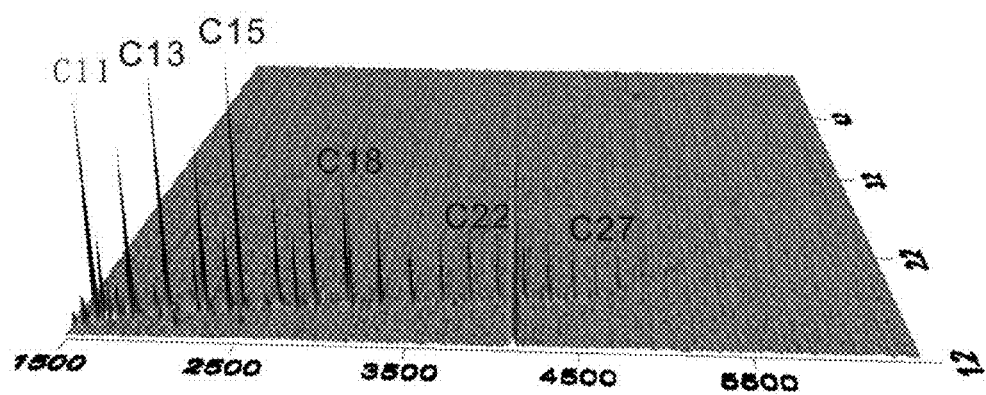
FIG. 9 shows an analysis result of the ingredients of the inclusion in Example 3 by comprehensive two-dimensional gas chromatography-time-of-flight mass spectrometry.

The ingredients of one and the same target inclusion in the sample 1 were collected on condition that the background ingredients thereof were not affected. That is, steps (1) to (5) were repeated. Chromatography-mass spectrometry analysis and comprehensive two-dimensional gas chromatography-time-of-flight mass spectrometry analysis on the ingredients of the inclusion were performed and the results thereof are shown in FIGS. 8 and 9, respectively.

Comparisons indicate similar distribution patterns between and among n-alkanes in detected ingredients of the inclusion.

The results show that the sample obtained by this method can undergo analysis implemented by two geometrical analysis instruments simultaneously. The operation can be simple and flexible with a rather small amount of outside contaminations introduced, and therefore can effectively collect ingredients with large numbers of carbon atoms in target inclusions.

As will be appreciated by one skilled in the art, the foregoing functions and/or process may be embodied as a system, method, or computer program product. For example, the functions and/or process may be implemented as computer-executable program instructions recorded in a computer-readable storage device that, when retrieved and executed by a computer processor, controls the computing system to perform the functions and/or process of embodiments described herein. In one embodiment, the computer system can include one or more central processing units, computer memories (e.g., read-only memory, random access memory), and data storage devices (e.g., a hard disk drive). The computer-executable instructions can be encoded using any suitable computer programming language (e.g., C++, JAVA, etc.). Accordingly, aspects of the present disclosure may take the form of an entirely software embodiment (including firmware, resident software, micro-code, etc.) or an embodiment combining software and hardware aspects.

From the above description, it is clear that the present disclosure is well adapted to carry out the objects and to attain the advantages mentioned herein as well as those inherent in the presently provided disclosure. While preferred embodiments of the present disclosure have been described for purposes of this disclosure, it will be understood that changes may be made which will readily suggest themselves to those skilled in the art and which are accomplished within the spirit of the present disclosure.

LIST OF REFERENCE NUMBERS

1: oil-bearing inclusion sample;
2: second square quartz capillary tube;
3: n-hexane (about 10 ul);
4: first square quartz capillary tube; and
5: depression structure of the second square quartz capillary tube.

The invention claimed is:

1. A method of sampling an oil-bearing inclusion, comprising:
    a) providing a first container and a second container, an external diameter of the first container being smaller than an internal diameter of the second container;
    b) adding a solvent into the first container and sealing the first container;
    c) adding an oil-bearing inclusion sample into the second container, putting the first container obtained from step b) into the second container, and then sealing the second container; and
    d) using a laser to ablate the oil-bearing inclusion sample contained in the second container obtained from step c) so as to release ingredients of the oil-bearing inclusion sample therein, and then using the laser to break the first container while the second container remains sealed so that the solvent in the first container enters the second container and dissolves at least a portion of the ingredients of said oil-bearing inclusion sample into the solvent.

2. The method according to claim 1, wherein the first container and the second container are independently made of at least one material selected from the group consisting of organic polymers and inorganic glass.

3. The method according to claim 2, wherein said organic polymer is at least one selected from the group consisting of polymethylmethacrylate, polypropylene, polycarbonate, polyethylene, polyamide, and polystyrene, while said inorganic glass is at least one selected from the group consisting of ordinary glass and quartz glass.

4. The method according to claim 1, wherein a cross section of the first container or the second container is in a shape selected from the group consisting of squares, triangles, ovals, circles, semicircles, and polygons.

5. The method according to claim 1, wherein a hydrogen flame gun is used in step b) and step c) for sealing the first container or the second container.

6. The method according to claim 1, wherein said solvent used in step b) is at least one selected from the group consisting of n-hexane, n-heptane, isooctane, isopropanol, dichloromethane, cyclohexane, benzene, toluene, freon, trichloromethane, and ether.

7. The method according to claim 1, wherein said solvent used in step b) is injected into the first container by a chromatography syringe, and then centrifuged to reach an end portion of the first container in a centrifuge, and the solvent is frozen into a solid, and wherein the first container is vacuum sealed.

8. The method according to claim 1, wherein step d) further comprises centrifuging the solvent entering the second container from the first container to concentrate the solvent in the end of the second container where the oil-bearing inclusion sample is located.

9. The method according to claim 1, wherein the oil-bearing inclusion sample obtained in step d) is analyzed with a geochemical instrument.

10. The method according to claim 1, further comprising forming a depression in said second container at a location between the oil-bearing inclusion sample and the first container.

* * * * *